United States Patent [19]
Cook et al.

[11] Patent Number: 5,874,630
[45] Date of Patent: Feb. 23, 1999

[54] SYNTHESIS OF MERCAPTANS FROM ALCOHOLS

[75] Inventors: Charles M. Cook, Williamsville; David E. Albright, Grand Island; Michael C. Savidakis, Niagara Falls, all of N.Y.

[73] Assignee: Occidental Chemical Corporation, Niagara Falls, N.Y.

[21] Appl. No.: 3,386

[22] Filed: Jan. 6, 1998

[51] Int. Cl.$^6$ .................................................. C07C 319/08
[52] U.S. Cl. ................................................. 568/71; 578/73
[58] Field of Search ......................................... 568/71, 73

[56] References Cited

U.S. PATENT DOCUMENTS

| | | |
|---|---|---|
| 2,786,079 | 3/1957 | Folkins . |
| 2,820,060 | 1/1958 | Folkins . |
| 2,820,061 | 1/1958 | Folkins et al. . |
| 2,829,272 | 10/1953 | Doumani . |
| 3,006,966 | 10/1961 | Doumani . |
| 3,035,097 | 5/1962 | Deger . |
| 3,053,902 | 9/1962 | Doumani . |
| 3,935,276 | 1/1976 | Biola . |
| 4,302,605 | 11/1981 | Buchholz ................................. 568/60 |
| 5,026,915 | 6/1991 | Buchholz ................................. 568/26 |
| 5,283,369 | 2/1994 | Clark et al. . |

FOREIGN PATENT DOCUMENTS 07 96656 A1   3/1997   European Pat. Off. .

OTHER PUBLICATIONS

An Article by C. Forguy et al., titled "Heterogenous Catalysis," (1988) pp. 91 to 104.

An Article by H.O. Folkins et al., in I&EC Process DeSign and Development, vol. I, No. 4 (Oct. 1962), pp. 271 to 274.

*Primary Examiner*—Gary Geist
*Assistant Examiner*—Jean F. Vollano
*Attorney, Agent, or Firm*—Richard D. Fuerle; Anne E. Brookes

[57] ABSTRACT

Disclosed is a method of making a mercaptan by reacting an aliphatic alcohol with hydrogen sulfide in a continuous gaseous phase reaction. The reaction is performed in the presence of a catalyst which comprises a catalytically active carrier that contains base and/or acid active sites, an alkali metal or alkaline earth metal bicarbonate, carbonate, oxide, or hydroxide, and a transition metal acid or alkali metal or alkaline earth metal salt thereof. Selectivities of close to 100% are obtained.

19 Claims, No Drawings

SYNTHESIS OF MERCAPTANS FROM ALCOHOLS

BACKGROUND OF THE INVENTION

This invention relates to a process for synthesizing mercaptans from alcohols and hydrogen sulfide. In particular, it relates to a novel catalyst for use in that process.

Mercaptans can be synthesized by reacting alcohols with hydrogen sulfide in the presence of a catalyst. Catalysts used for this reaction have included bases such as potassium hydroxide and transition metal oxides, such as $K_2WO_4$, on an alumina substrate. These catalysts can produce selectivities as high as 95% for the conversion of methanol to methyl mercaptan, but conversions of higher molecular weight alcohols to mercaptans are substantially lower. Alcohol that is not converted to mercaptan is converted into undesired byproducts, such as alkenes, ethers, and sulfides; unreacted alcohol may also be present in the product mixture. Not only is this a waste of alcohol, but it is usually necessary to separate the desired mercaptan from these byproducts, which may be difficult since an azeotrope may exist between the alcohol and the mercaptan. This adds an additional expensive step to the production process.

SUMMARY OF THE INVENTION

We have discovered novel catalysts for reacting alcohols with hydrogen sulfide to produce mercaptans that, unlike prior art catalysts, have selectivities of very close to 100%. Products can be produced in accordance with the process of this invention that are so pure that purification requirements are minimal.

DESCRIPTION OF THE PREFERRED EMBODIMENTS

In the process of this invention an alcohol is reacted with a stoichiometric amount of hydrogen sulfide in the presence of a catalyst to produce a mercaptan and water:

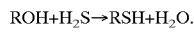

$$ROH + H_2S \rightarrow RSH + H_2O.$$

The use of excess hydrogen sulfide can be beneficial as it may reduce sulfide formation. The R group is aliphatic from $C_1$ to $C_{14}$ and can include atoms such as oxygen, sulfur, and silicon. Preferably, R is $C_6$ to $C_{12}$ as alcohols containing more than 12 carbon atoms are hard to volatilize without decomposition occurring and it is usually uneconomical to produce mercaptans by this process from alcohols containing fewer than 6 carbon atoms. Preferably, R is a hydrocarbon as those alcohols may be easier to volatilize and are less susceptible to side reactions. A mono, di, or polyhydroxy alcohol can be used, which can be straight chain or branched. Primary alcohols are preferred because there are fewer byproducts. Examples of alcohols that can be used in this invention include n-propanol; n-butanol; sec-butanol; n-hexanol; n-pentanol; 2-ethylhexanol; n-octanol; n-decyl alcohol; n-dodecyl alcohol; mercaptoethanol; ethylene glycol; 1,3-propanediol; 1,6-hexane diol; and cyclohexanol. The preferred alcohols are n-octanol and n-dodecyl alcohol because the mercaptans made from those alcohols are commercially important.

The catalyst used in the process of this invention has three components—a support, a base, and a transition metal compound. The support is a catalytically active carrier that contains base and/or acid active sites. Examples of suitable supports include alumina, zirconia, silica, titania, alumina-silicates (zeolites), and magnesia-aluminates. Alumina is preferred because it has more surface area and active sites, thus giving higher selectivities and conversions. Especially preferred is a mixed phase alumina of the chi, eta, and rho phases as it enhanced the performance of all the catalysts tested. The carrier preferably has a surface area of about 100 to about 400 $m^2/g$ as carriers with less surface area are less active and carriers with more surface area are very difficult to obtain.

The base is an alkali metal or alkaline earth metal bicarbonate, carbonate, oxide, or hydroxide. Alkali metal bases and hydroxides are preferred as they work better. Examples of suitable bases include sodium hydroxide, potassium hydroxide, magnesium hydroxide, calcium hydroxide, sodium bicarbonate, sodium carbonate, magnesium oxide, and calcium oxide. The preferred bases are potassium hydroxide and rubidium hydroxide as they had very high selectivity. (Rubidium oxide can be used to form rubidium hydroxide in situ by reaction with water, if desired.) It is critical to the success of the process of this invention in producing very high selectivity and conversion that an excess of base over stoichiometric be present. The amount of excess base should be 0.1 to 10 wt % over the stoichiometric amount required to react with the transition metal compound. If less base is used, the selectivity will be reduced, and more base will reduce the activity. The preferred amount of excess base is 0.5 to 1 wt % in excess of stoichiometric.

The transition metal compound is an acid or an alkali metal or alkaline earth metal salt thereof. The transition metals are Groups 3 to 12 in the Periodic Table and include tungsten, molybdenum, chromium, manganese, titanium, zirconium, cobalt, and nickel. Tungsten is the preferred transition metal as its compounds have been found to work the best. Examples of suitable transition metal compounds include $WO_3$, $K_2WO_4$, $Na_2WO_4$, $MoO_3$, $K_2MoO_4$, $Na_2MoO_4$, phosphotungstate, phosphomolybdate, and silicotungstate. The preferred transition metal compound is either $WO_3$ or $K_2WO_4$. The amount of transition metal compound should be about 1 to about 20 wt %, based on the carrier weight, as less transition metal compound reduces the selectivity and more reduces the activity of the catalyst; preferably, the transition metal compound should be about 3 to about 5 wt % of the carrier weight. However, if the base is a rubidium compound, a transition metal compound is unnecessary and is preferably not used.

The amount of catalyst (i.e., carrier plus transition metal compound plus base) should be such that about 0.4 to about 8 g of the alcohol pass over each gram of the catalyst per hour. At a slower rate, an excessively large reactor would be required, and a faster rate may result in an incomplete conversion of the alcohol to the mercaptan. Preferably, about 1 to about 4 g of alcohol should pass over each gram of the catalyst every hour.

The catalyst can be prepared in the same way that prior art catalysts are prepared for this reaction. For example, the carrier, transition metal compound, and base can be mixed into a paste, extruded, and calcined. Another procedure for catalyst preparation is to dissolve the transition metal compound and the base in a solvent such as water, and spray the resulting solution onto the powdered carrier. This is again followed by calcining.

The reaction of the alcohol with the hydrogen sulfide to produce the mercaptan is a gas phase reaction. The alcohol and hydrogen sulfide are normally heated to a temperature high enough to volatilize both the alcohol and the product mercaptan. However, care should be taken that the temperature is not so high that the mercaptan is decomposed. While the particular temperature range will depend upon the mercaptan that is being made, in general, a temperature range between about 250° and about 450° C. is appropriate. Temperatures below about 250° C. should be avoided as undesirable reactions may occur. Temperatures above 450° C. should be avoided as olefin formation can become significant at those temperatures. Pressures from atmospheric up to about 500 psi can be used. It is preferable to use the highest pressure at which the feed and the product do not condense as high pressures produce high conversions and selectivities. The reaction is performed continuously. Upon completion of the reaction, the water formed is separated, typically by phase separation (decanting). Since the process of this invention can produce selectivities of very close to 100%, it is often not necessary to purify the product, but, if desired, purification can be performed by distillation or other procedures. The products are used commercially in polymers and lubricants, and as chemical intermediates.

The following examples further illustrate this invention.

EXAMPLES

Experiments were conducted in a ½" diameter 316 stainless steel tube about 14" in length fitted with a catalyst support screen and internal thermocouple. Approximately 26 cc of catalyst were charged for each reaction. The tube temperature was controlled by an external electric heating mantle. Octanol was metered at 0.3 g/min. into a flowing stream of hydrogen sulfide and volatilized in a preheater before entering the catalyst reactor. Hydrogen sulfide flow rate was controlled to conduct a series of tests in the range of 1 to 10 molar equivalents. Reactor pressure was controlled by an outlet control valve to conduct a series of experiments in the range of 0 to 100 psig. Reaction products were collected in a stainless steel receiver. Samples from various operating conditions were analyzed by gas chromatography to determine mercaptan, sulfide, ether, olefin, and unreacted octanol content. No other significant impurities were detected. The following table gives the reactants, reaction conditions, and results.

In these examples, the selectivity is the moles of the desired mercaptan product divided by the moles of alcohol converted into some product. The conversion is the moles of alcohol reacted divided by the moles of alcohol fed into the reactor. Examples 1 to 17 are comparative examples and Examples 18 to 23 illustrate the method of this invention.

| | | | | | Residence | GC Area % | | | | | | | |
| | | | | | | 1.3 min | 3.9 min | 4.7 min | 5.4 min | 6.6 min | | | RSH |
| No. | Catalyst | Temp. (°C.) | Pressure (psig) | $H_2S$ (sccm) | Time (s) | Octenes | R-SH | R-OH | Ether | Sulfide | Others | Conv. | Selectivity | Yield % |
|---|---|---|---|---|---|---|---|---|---|---|---|---|---|---|
| 1 | 3% Potassium (as KOH) on Alumina (1) | 350 | 100 | 300 | 15.15 | 9.5 | 66.4 | 0 | 0 | 4.1 | 0 | 100 | 86.4 | 86.4 |
| 2 | 12% $K_2WO_4$ on Alumina (2) | 378 | 70 | 300 | 10.71 | 7 | 74.5 | 14.1 | 0 | 2.7 | — | 85.9 | 86.7 | 74.5 |
| 3 | CaO on Alumina (3) | 347 | 0 | 600 | 1.05 | 9.4 | 76 | 7.6 | — | 4.5 | — | 92.4 | 82.3 | 76 |
| 4 | 3% Li (as LiOH) on Alumina (1) | 351 | 45 | 300 | 7.67 | 9.4 | 73.4 | 8.4 | — | 7.1 | — | 91.6 | 80.1 | 73.4 |
| 5 | 3% Titanium (Ti) on Alumina (1) | 350 | 100 | 300 | 15.15 | 14.2 | 73.1 | 0 | 0 | 12.7 | 0 | 100 | 73.1 | 73.1 |
| 6 | 3% KOH on Alumina (4) | 350 | 0 | 150 | 3.38 | 14.6 | 72.7 | 9.8 | — | 1.5 | — | 90.2 | 80.6 | 72.7 |
| 7 | 3% Titanium (Ti) and 0.5% KOH on Alumina (1) | 350 | 100 | 300 | 15.15 | 15.1 | 70.9 | 0 | 0 | 13.9 | 0 | 100 | 70.9 | 70.9 |
| 8 | Alumina (1) | 366 | 0 | 850 | 0.74 | 23.7 | 69.7 | 2.8 | — | 12.5 | — | 97.2 | 71.7 | 69.7 |
| 9 | 3% Zirconium (Zr) on Alumina (1) | 325 | 50 | 300 | 6.90 | 15.5 | 69.3 | 0 | 0 | 15.2 | 0 | 100 | 69.3 | 69.3 |
| 10 | 2—4% NaO on Alumina (5) | 364 | 80 | 300 | 12.24 | 10.7 | 64.9 | 11.9 | — | 4.3 | — | 88.1 | 73.7 | 64.9 |
| 11 | 3% Lithium (as LiOH) on Alumina (6)/2% Carbon | 350 | 50 | 300 | 8.55 | 6.5 | 60.7 | 24.6 | 0 | 6.1 | 0 | 75.4 | 80.5 | 60.7 |
| 12 | 2% Laz on Alumina (1) | 350 | 50 | 300 | 8.55 | 23.5 | 62.3 | 0.6 | 0 | 12.6 | — | 99.2 | 62.8 | 62.3 |
| 13 | Alumina Cut Rings (7) | 300 | 100 | 300 | 16.48 | 48.3 | 38.4 | 0 | 0 | 9.3 | 3.9 | 100 | 38.4 | 38.4 |
| 14 | Co/Mo (8) on Alumina | 280 | 0 | 160 | 3.63 | 38.2 | 36.1 | 6.8 | 6.3 | 5.4 | — | 93.2 | 38.7 | 36.1 |
| 15 | $K_2O$ on Silica (9) | 350 | 0 | 300 | 1.94 | 2.9 | 25.3 | 61.7 | 0 | 6.5 | 0 | 34.7 | 72.9 | 25.3 |
| 16 | Alumina (6)/2% Carbon | 350 | 0 | 150 | 3.38 | 70.8 | 25.2 | 0 | 0 | 4 | 0 | 100 | 25.2 | 25.2 |
| 17 | 4% $K_2WO_4$/0.7% KOH on Alumina (6) | 350 | 100 | 300 | 15.2 | 32 | 49.6 | 5.9 | 0.8 | 9.9 | 1.9 | 94.1 | 52.7 | 49.6 |
| 18 | 4% $K_2WO_4$/0.7% KOH on Alumina (1) | 300 | 100 | 300 | 16.48 | 0 | 100 | 0 | 0 | 0 | 0 | 100 | 100.0 | 100 |
| 19 | 5% $K_2WO_4$/1% KOH on Alumina (1) | 350 | 100 | 300 | 15.15 | 0 | 88.8 | 11.2 | 0 | 0 | 0 | 88.8 | 100.0 | 88.8 |
| 20 | 4% $K_2WO_4$ + 0.7% KOH on Alumina (7) | 350 | 100 | 300 | 15.15 | 32 | 49.6 | 5.9 | 0.8 | 9.9 | 1.9 | 94.1 | 52.7 | 49.6 |
| 21 | Tungstic Acid ($H_2WO_4$) on CaO/Alumina (3) | 325 | 100 | 300 | 15.79 | 0 | 78.4 | 16.6 | 0 | 5 | 0 | 83.4 | 94.0 | 78.4 |
| 22 | 3% $Rb_2WO_4$ + 3% RbOH on Alumina (1) | 350 | 100 | 300 | 15.15 | 3.2 | 92.3 | 0 | 0 | 4.5 | 0 | 100 | 92.3 | 92.3 |
| 23 | 3% Rb (as RbOH) on Alumina (1) | 350 | 100 | 300 | 15.15 | 3.5 | 91.2 | 0 | 0 | 5.3 | 0 | 100 | 91.2 | 91.2 |

(1). Mixed phase chi eta rho alumina sold by Alcoa as "DD-422"
(2). Sold by UOP as "9242-06"
(3). Sold by Alcoa as "DD-831"
(4). Sold by UOP as "9242-04"
(5). Sold by Alcoa as "DD-710"
(6). Gamma alumina sold by Engelhard as "Al-3438"
(7). Gamma alumina sold by Engelhard as "Al-3996"
(8). Sold by United Catalyst as "C-20"
(9). Sold by Engelhard as "N7014"

The table shows that some of the examples performed according to the method of this invention (i.e., Examples 18 and 19) were superior to the comparison examples in that they had the selectivities of 100% and high conversions. A comparison of Examples 18 and 20 shows that the alumina used significantly affects the conversion. A comparison of Examples 17 and 18 shows that even under the exact same doping, mixed phase chi eta rho alumina had better selectivity than gamma alumina.

We claim:

1. A method of making a mercaptan comprising passing over each gram of a catalyst about 0.4 to about 8 g per hour of a vaporized alcohol having the formula ROH and at least about a stoichiometric amount of gaseous hydrogen sulfide, where said catalyst comprises
   (1) mixed phase chi eta rho alumina;
   (2) a transition metal compound selected from the group consisting of transition metal acids and alkali metal or alkaline earth metal salts thereof, in an amount of 0 to about 20 wt %, based on the weight of said mixed phase chi eta rho alumina; and
   (3) an alkali metal or alkaline earth metal bicarbonate, carbonate, oxide, or hydroxide, in an amount of about 0.1 to about 10 wt % in excess of the amount needed to stoichiometrically react with said transition metal compound, where R is aliphatic from $C_1$ to $C_{14}$.

2. A method according to claim 1 wherein R is a hydrocarbon having 6 to 12 carbon atoms.

3. A method according to claim 2 wherein said alcohol is a primary alcohol.

4. A method according to claim 3 wherein said alcohol is 2-ethylhexanol.

5. A method according to claim 3 wherein said alcohol is n-octanol.

6. A method according to claim 3 wherein said alcohol is n-dodecyl alcohol.

7. A method according to claim 1 wherein transition metal is tungsten.

8. A method according to claim 1 wherein said mixed phase chi eta rho alumina has a surface area of about 100 to about 400 $m^2/g$.

9. A method according to claim 1 wherein said base is a hydroxide.

10. A method according to claim 9 wherein said base is potassium hydroxide.

11. A method according to claim 1 wherein said base is rubidium hydroxide, rubidium oxide, or mixtures thereof.

12. A method according to claim 1 wherein said transition metal compound is $WO_3$ or $K_2WO_4$.

13. A method of making a mercaptan comprising passing over each gram of a catalyst about1 to about 4 g per hour of a vaporized primary alcohol having the formula ROH and at least about a stoichiometric amount of gaseous hydrogen sulfide, where said catalyst comprises
   (1) mixed phase chi eta rho alumina having a surface area of about 100 to about 400 $m^2/g$;
   (2) 0 to about 20 wt %, based on the weight of said mixed phase chi eta rho alumina, of a tungsten compound selected from the group consisting of tungstic acid and alkali metal and alkaline earth metal salts thereof; and
   (3) an alkali metal hydroxide, in an amount of about 0.5 to about 1 wt % in excess of the amount needed to stoichiometrically react with said tungsten compound, where R is hydrocarbon from $C_6$ to $C_{12}$.

14. A method according to claim 13 wherein said alcohol is 2-ethylhexanol.

15. A method according to claim 13 wherein said alcohol is n-octanol.

16. A method according to claim 13 wherein said alcohol is n-dodecyl alcohol.

17. A method according to claim 13 wherein said alkali metal hydroxide is potassium hydroxide or rubidium hydroxide.

18. A method according to claim 13 wherein said tungsten compound is $WO_3$ or $K_2WO_4$.

19. A method of making a mercaptan comprising passing over each gram of a catalyst 1.0 to 4.0 g per hour of a vaporized alcohol selected from the group consisting of n-hexanol, n-octanol, and n-dodecyl alcohol and at least about a stoichiometric amount of gaseous hydrogen sulfide, where said catalyst comprises
   (1) mixed phase chi eta rho alumina having a surface area of about 100 to about 400 $m^2/g$;
   (2) 0 to about 20 wt %, based on the weight of said alumina, of $WO_3$ or $K_2WO_4$; and
   (3) potassium hydroxide or rubidium hydroxide, in an amount of about 0.5 is to about 1 wt % in excess of the amount needed to stoichiometrically react with said $WO_3$ or $K_2WO_4$.

* * * * *